(12) United States Patent
Kessler et al.

(10) Patent No.: US 10,352,868 B2
(45) Date of Patent: Jul. 16, 2019

(54) GRADING LAMP FOR GEMSTONES

(71) Applicant: Sy Kessler Sales, Inc., Dallas, TX (US)

(72) Inventors: Daniel L. Kessler, Dallas, TX (US);
Henry M. Kessler, Dallas, TX (US)

(73) Assignee: Sy Kessler Sales, Inc., Dallas, TX (US)

( * ) Notice: Subject to any disclaimer, the term of this patent is extended or adjusted under 35 U.S.C. 154(b) by 0 days.

(21) Appl. No.: 15/637,739

(22) Filed: Jun. 29, 2017

(65) Prior Publication Data

US 2018/0003646 A1  Jan. 4, 2018

Related U.S. Application Data

(60) Provisional application No. 62/355,981, filed on Jun. 29, 2016.

(51) Int. Cl.
| | |
|---|---|
| *G01N 21/87* | (2006.01) |
| *B65D 1/36* | (2006.01) |
| *B65D 43/16* | (2006.01) |
| *B65D 51/24* | (2006.01) |
| *G01N 21/88* | (2006.01) |

(52) U.S. Cl.
CPC .............. *G01N 21/87* (2013.01); *B65D 1/36* (2013.01); *B65D 43/163* (2013.01); *B65D 51/248* (2013.01); *G01N 21/8806* (2013.01)

(58) Field of Classification Search
CPC ...... G01N 21/87; G01N 21/8806; B65D 1/34; B65D 1/36; B65D 43/163; B65D 51/248; G01B 33/381
See application file for complete search history.

(56) References Cited

U.S. PATENT DOCUMENTS

| | | | |
|---|---|---|---|
| 3,944,368 A | 3/1976 | Beesley | |
| 3,950,102 A * | 4/1976 | Eickhorst | G01N 21/6447 356/73 |
| 4,012,141 A | 3/1977 | Hanneman | |
| 4,291,975 A | 9/1981 | Raccah | |
| 4,461,568 A | 7/1984 | Welbourn et al. | |
| 4,534,644 A * | 8/1985 | Beesley | G01J 3/52 356/30 |
| 4,906,093 A | 3/1990 | Trossarelli | |
| 5,143,212 A * | 9/1992 | Roberts | G01J 3/52 206/223 |

(Continued)

FOREIGN PATENT DOCUMENTS

WO    WO2016/055843 A1 * 10/2014

OTHER PUBLICATIONS

GemOro CZ Master Set Pro, The Bell Group, Inc. 2011.*

*Primary Examiner* — Dominic J Bologna
(74) *Attorney, Agent, or Firm* — Scott T. Griggs; Griggs Bergen LLP

(57) ABSTRACT

A grading lamp for gemstones is disclosed. In one embodiment, the grading lamp includes a base having an open top with a bottom wall bounded by upstanding front, rear, and side walls, and a lid hinged to the rear wall for swinging between open, intermediate, and closed positions relative to the base. The lid includes an interior lamp recess having natural and ultraviolet lights behind a light diffusing filter. A tray within the open top of the base holds color reference stones and a gem under examination. In the intermediate position, the grading lamp mitigates outside ambient light and provides direct light from either the natural or ultraviolet lights.

18 Claims, 2 Drawing Sheets

(56) References Cited

U.S. PATENT DOCUMENTS

| | | |
|---|---|---|
| 5,615,005 A | 3/1997 | Valente et al. |
| 6,020,954 A | 2/2000 | Aggarwal |
| 6,473,164 B1 * | 10/2002 | De Jong ................ G01N 21/87 356/30 |
| 6,980,283 B1 | 12/2005 | Aggarwal |
| 7,102,742 B2 | 9/2006 | Geurts |
| 2007/0067178 A1 | 3/2007 | Reinitz et al. |
| 2007/0296954 A1 | 12/2007 | Geurts |

* cited by examiner

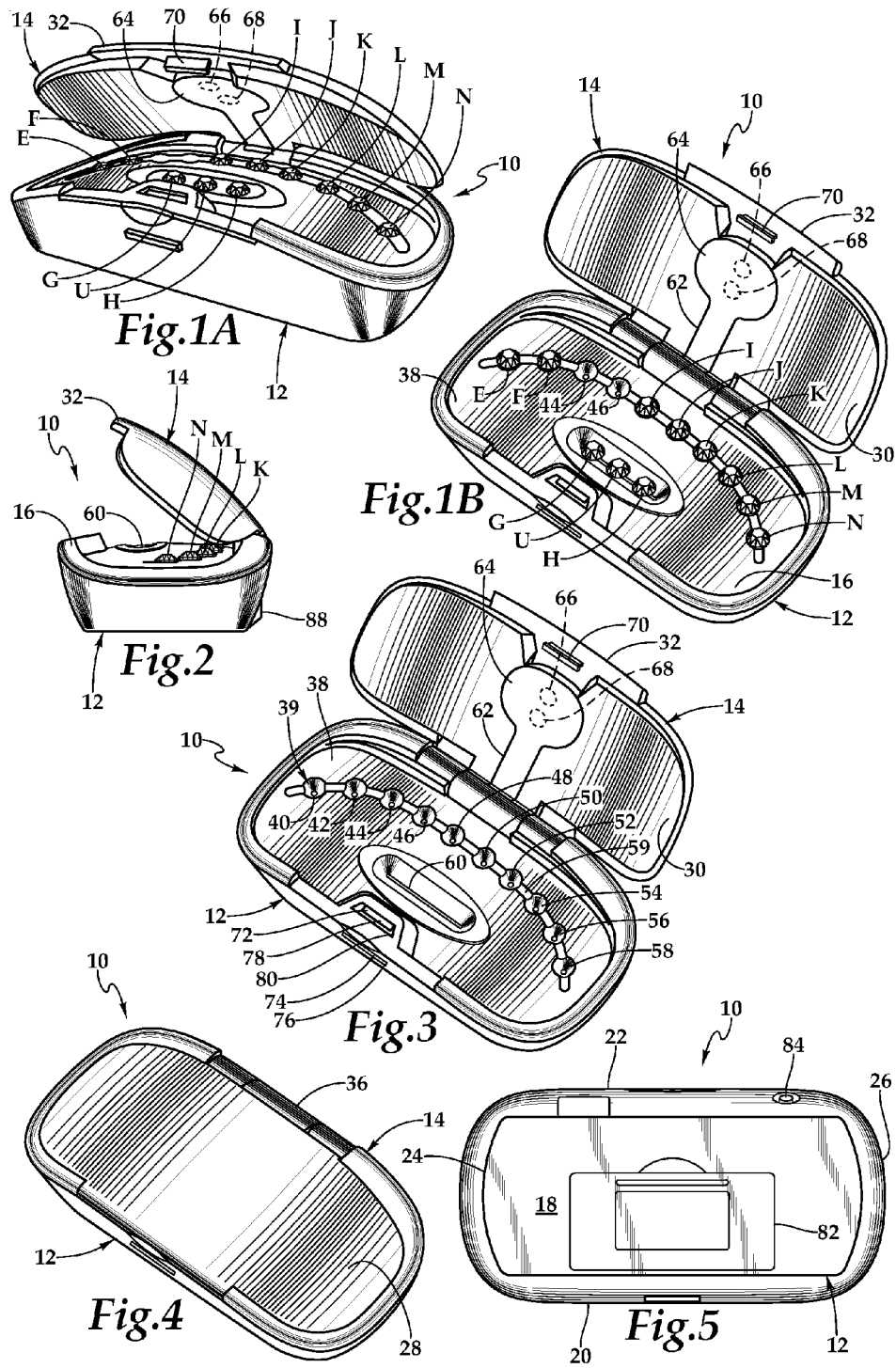

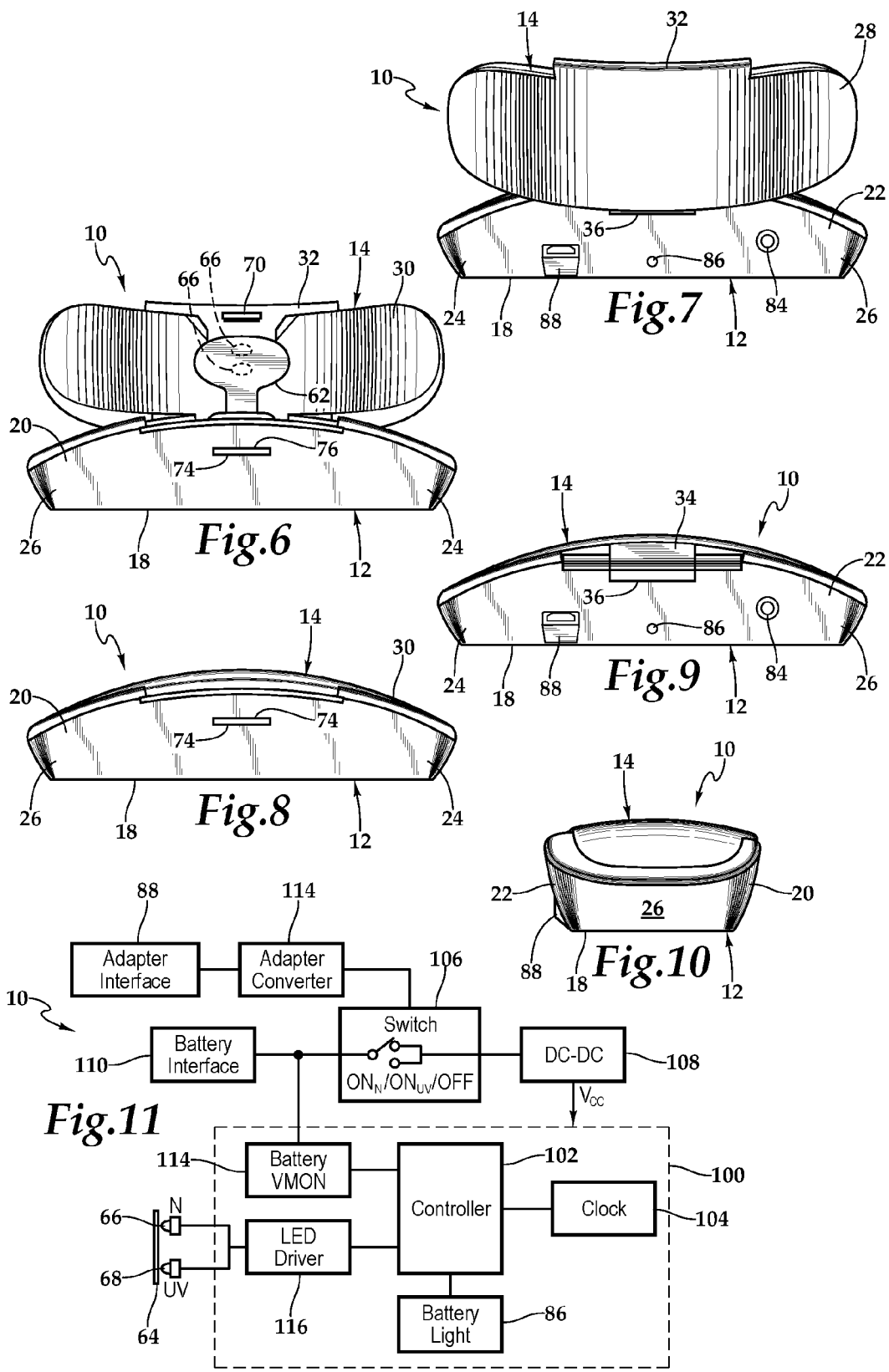

US 10,352,868 B2

GRADING LAMP FOR GEMSTONES

PRIORITY STATEMENT

This application claims priority from U.S. patent application Ser. No. 62/355,981 entitled "Grading Lamp for Gemstones" and filed on Jun. 29, 2016 in the names of Daniel L. Kessler and Henry M. Kessler; which is hereby incorporated by reference for all purposes.

TECHNICAL FIELD OF THE INVENTION

This invention relates, in general, to the identification of precious diamonds and, in particular, to grading lamps for distinguishing gemstones such as diamonds on the basis of color as recognized by a grading scale used by internationally recognized laboratories.

BACKGROUND OF THE INVENTION

Without limiting the scope of the invention, its background is described in connection with diamonds, as an example. The degree to which diamonds exhibit body color is one of the four value factors by which diamonds are assessed. Diamonds have a color grading system that refers to the absence of color. In internationally recognized laboratories such as the Gemological Institute of America (GIA), this system goes from D to Z. In general, the more colorless a diamond, the rarer and more valuable the diamond is because it appears white and brighter to the eye. Advances in instruments and techniques are required to improve color recognition and grading of diamonds.

SUMMARY OF THE INVENTION

It would be advantageous to achieve advances in instruments to authenticate diamonds in order to improve color assessment and grading. It would also be desirable to enable an electro-mechanical solution that would improve operator technique when grading diamonds. To better address one or more of these concerns, a grading lamp for gemstones is disclosed. In one embodiment, the grading lamp includes a base having an open top with a bottom wall bounded by upstanding front, rear, and side walls, and a lid hinged to the rear wall for swinging between open, intermediate, and closed positions relative to the base. The lid includes an interior lamp recess having natural daylight and ultraviolet light behind a light diffusing filter. A tray within the open top of the base holds color reference stones and a gem under examination. In the intermediate position, the grading lamp mitigates outside ambient light and provides direct light from either the natural daylight or ultraviolet light. These and other aspects of the invention will be apparent from and elucidated with reference to the embodiment described hereinafter.

BRIEF DESCRIPTION OF THE DRAWINGS

For a more complete understanding of the features and advantages of the present invention, reference is now made to the detailed description of the invention along with the accompanying figures in which corresponding numerals in the different figures refer to corresponding parts and in which:

FIG. 1A is a front perspective view of one embodiment of the grading lamp presented according to the teachings presented herein, wherein a gemstone under test is being compared utilizing comparison stones and the grading lamp is in an intermediate position;

FIG. 1B is a top perspective view of the grading lamp depicted in FIG. 1A, wherein a gemstone under test is being compared utilizing comparison stones;

FIG. 2 is a side elevation view of the grading lamp of FIG. 1A, wherein a gemstone under test is being compared utilizing comparison stones;

FIG. 3 is a top perspective view of the grading lamp depicted in FIG. 1A, wherein the grading lamp is in an open position, without the gemstone under test or the comparison stones;

FIG. 4 is a top perspective view of the grading lamp depicted in FIG. 3, wherein the grading lamp is in a closed position;

FIG. 5 is a bottom plan view of the grading lamp depicted in FIG. 3, wherein the grading lamp is in a closed position;

FIG. 6 is a front elevation view of the grading lamp depicted in FIG. 3, wherein the grading lamp is in an open position;

FIG. 7 is a rear elevation view of the grading lamp depicted in FIG. 3, wherein the grading lamp is in an open position;

FIG. 8 is a front elevation view of the grading lamp depicted in FIG. 3, wherein the grading lamp is in a closed position;

FIG. 9 is a rear elevation view of the grading lamp depicted in FIG. 3, wherein the grading lamp is in a closed position;

FIG. 10 is a right side elevation view of the grading lamp depicted in FIG. 3, wherein the grading lamp has left-right symmetry and the grading lamp is in a closed position; and FIG. 11 is a schematic functional block diagram of one embodiment of the grading lamp.

DETAILED DESCRIPTION OF THE INVENTION

While the making and using of various embodiments of the present invention are discussed in detail below, it should be appreciated that the present invention provides many applicable inventive concepts which can be embodied in a wide variety of specific contexts. The specific embodiments discussed herein are merely illustrative of specific ways to make and use the invention, and do not delimit the scope of the present invention.

Referring initially to FIG. 1A through FIG. 10, therein is depicted a grading lamp for gemstones, such as diamonds, that is schematically illustrated and generally designated 10. The grading lamp 10 includes a base 12 and a lid 14. The base 12 has an open top 16 with a bottom wall 18 bounded by upstanding front wall 20, rear wall 22, and sidewalls 24, 26. The lid 14 has an upper surface 28 and a lower surface 30 bounded by depending front and rear flanges 32, 34, respectively. The rear wall 22 of the base 12 and the rear flange 34 of the lid 14 are pivotally connected by a hinge 36 which supports the lid 14 on the base 12 for swinging movement between an open position (e.g., FIGS. 1B, 3, and 6-7), wherein the lid 14 is disposed in a generally erect attitude over the rear wall 22 of the base 12 and a closed position (e.g., FIGS. 4-5 and 8-10) such that the lid 14 closes the open top 16 of the base 12. The lid 14 is swingable through and stoppable at an intermediate position (e.g., FIGS. 1A and 2), between its open and closed positions, wherein the lid 14 slopes forwardly and upwardly relative to the base 12. In one embodiment, the intermediate position may include the lid 14 sloping between 25 degrees and 65 degrees with respect to the base 12. In another embodiment, the intermediate position may be about 45 degrees with respect to the base 12. The grading lamp 10 may be handheld and constructed of lightweight materials with weights added to the interior of the base 12 to increase heft.

In one embodiment, disposed within the open top 16 of the base 12 is a tray 38 including multiple reference stone receptacles 39 shown as ten depressed cones 40, 42, 44, 46, 48, 50, 52, 54, 56, 58. In one implementation, each cone 40-58 is sized to hold a 0.5 to 1.0 carat reference stone corresponding to the standard GIA diamond color grading scale providing comparison points of D, E, F, G, H, I, J, K, L, M, and/or N, for example. It should be appreciated that although a standard GIA diamond color grading scale is presented herein, any diamond color grading scale or portion thereof, standard or non-standard, may be implemented with any set of comparison points, including initial and final comparison points. It should be further appreciated that the multiple reference stone receptacles 39 may have a variety of spatial form factors for accepting a variety of color reference stones. Further, the number and placement of the reference stone receptacles 39 may vary. In FIGS. 1A, 1B, and 2, the references stones are labeled E, F, G, H, I, J, K, L, M, and N. Further, each of the cones 40-58 may be labeled E through N, respectively. In one implementation, the reference stone receptacles 39 may be molded into the tray 38 and labeling may accomplished through molding or laser inscription of the corresponding diamond colors on the tray 38 at the appropriate cones 40-58, for example. A channel 59 interconnects the reference stone receptacles 39 to provide space to facilitate the insertion and removal of the color reference stones therewith. The tray 38 also includes an examination receptacle 60, which in one embodiment, may be sized for at least two color reference stones and one gem under examination, which in FIGS. 1A, 1B, and 2, is labeled U. The tray may include a UV-inhibiting composition providing a substantially bright white color that will not "yellow" over time and prolonged exposure to UV-light.

Formed in and opening through the lower surface 30 of the lid 14 is a lamp recess 62 that is bounded by a light diffusing filter 64 that may be flush with the lower surface 30 of the lid 14. Lights 66, 68, which may be light emitting diodes (LEDs), are housed within the lamp recess 62 and supported by electronics (not shown) housed within the base 12. In one embodiment, the lights 66, 68 include a natural daylight providing LED and an ultraviolet (UV) light providing LED. The light diffusing filter 64 may soften the light intensity and properly disperse the light over the tray 38. It should be appreciated that in some embodiments, only the light 66 or the light 68 is provided. Further, one or both of the lights 66, 68 may be located on the lower surface 30 of the lid 14 without the lamp recess 62 and without the light diffusing filter 64.

Mounted on the front flange 32 of the lid 14 is a tab 70. A latch 72 is secured within the base 12 with a button 74 extending through an opening 76 in the front wall 20 and a catch arm 78 accessible through an opening 80 in the tray 38. The tab 70 mates with the latch 72 such that the lid 14 may be securely engaged with the base 12 in its closed position and releasably locked to provide for the intermediate position or the open position.

A battery door 82 is located within the bottom wall to provide access to a battery compartment having connections for multiple batteries in one embodiment. The batteries may be AAA batteries, lithium polymer batteries, rechargeable NiMH AAA batteries, or other battery or batteries that are non-rechargeable or recharged during plugged-in use of the grading lamp 10. if rechargeable batteries are utilized, a battery charging circuit (not shown) would be included. A power button 84 is located within the rear wall 22 of the base 12. In one implementation, the power button 84 cycles the grading lamp 10 through ON—natural daylight ($ON_N$), ON—ultraviolet light ($ON_{UV}$), and OFF modes of operation. A batter light 86 provides a low battery warning light if the batteries within the battery compartment behind the battery door 82 have depleted power. An adapter interface, which may be a USB or micro-USB interface, is also provided in the rear wall 22.

FIG. 11 depicts one embodiment of the grading lamp 10 in further detail. A circuit portion 100, including a controller 102, may include a microprocessor operating under the frequency source of a clock 104, to process a number of analog voltages at inputs to produce a number of outputs (discussed below) indicative of the mode of operation, i.e., $ON_N$ or $ON_{UV}$. A switch 106, which may be a single pole multiple throw mechanical switch operates under the actuation of the power button 84, controls the $ON_N$/$ON_{UV}$/OFF state of grading lamp 10 and the application of voltage to a DC-DC converter 108. A voltage source may be a battery interface 110 connected to the battery source, regular or rechargeable, or wall power provided by a wall adapter converter 112 and adapter interface 88. The low voltage DC-DC converter 108 converts the battery source or voltage supplied by the adapter converter 112 to an acceptable voltage for powering analog and digital circuitry. A battery voltage monitor 114 is provided to detect a low voltage condition in the battery source and communicate this information to the controller 102 and onto the battery light 86. The DC-DC converter 108 and a monitor circuit 114 are designed to condition the signal for processing within the controller 102. If low voltage condition is detected, the battery light 86 may provide an indication of faulty voltage while testing is temporarily suspended by the grading lamp 10.

An LED driver 116 controls lights 66, 68 in response to receiving signals from the controller. In one implementation, the light 66 provides a natural working light (N) and the other light 68 provides a UV working light (UV). It should be appreciated that the circuit design and architecture depicted in FIG. 11 is only exemplary and illustrative. Other designs and architectures are within the teachings presented herein.

With respect to one operational embodiment, as mentioned, the grading lamp 10 includes the base 12 having the open top 16 with the bottom wall 18 bounded by the upstanding front 20, rear 22, and side walls 24, 26, and the lid 14 is hinged to the rear wall for swinging between open, intermediate, and closed positions relative to the base 12. To open the grading lamp 10, the button 74 is pressed, while pulling open the lid 14 up and open with the other available hand. The lid 14 of the grading lamp 10 may be set to the intermediate position, which is from about 25 degrees to about 65 degrees with respect to the base 12. In a further embodiment, the lid 14 may be set to about 45 degrees with respect to the base 12. The intermediate position is configured to mitigate at the examination receptacle 60 ambient light sourced outside of the grading lamp 10 and to block at the examination receptacle 60 direct overhead light sourced outside of the grading lamp 10. The intermediate position is also configured to provide at the examination receptacle 60 direct light from the lights 66, 68. The natural daylight 66 provides appropriate lighting at the appropriate color temperature for diamond and gemstone color grading and color comparison. The UV light 68 provides the appropriate lighting at the appropriate color temperature for identifying fluorescence characteristics found in some diamonds and colored gemstones. The selection of natural daylight 66 or UV light 68 may be made by cycling the power button 84.

To color grade a gem under test U, which may be a diamond, the gem under test U is placed in the examination receptacle 60 at about a 45 degree angle, while setting the table of the gem under test U against the front of the examination receptacle 60, which may have a groove to assist with the placement of thereof. The natural daylight 66 may be selected for color grading and the UV light 68 may be selected for grading fluorescence. By process of elimination, the references stones E through N are placed adjacent to the gem under test U until a visual match is made. By way of example, with reference to FIGS. 1A, 1B, and 2, the gem under test U is being compared to the color reference stones G, H. When the color comparison is complete, the color reference stones E-N are returned to the respective cones 40-58 and the gem under test U may be removed. The power button 84 is pressed so that the grading lamp 10 is OFF. The button 74 is then pressed while the lid is closed onto the base 12. The closed position is configured to provide reference stone space contact between the lower surface 30 and the tray 38 such that the color reference stones E-N are held in place within the respective depressed cones 40-58 within the grading lamp 10.

The order of execution or performance of the methods and data flows illustrated and described herein is not essential, unless otherwise specified. That is, elements of the methods and data flows may be performed in any order, unless otherwise specified, and that the methods may include more or less elements than those disclosed herein. For example, it is contemplated that executing or performing a particular element before, contemporaneously with, or after another element are all possible sequences of execution.

While this invention has been described with reference to illustrative embodiments, this description is not intended to be construed in a limiting sense. Various modifications and combinations of the illustrative embodiments as well as other embodiments of the invention, will be apparent to persons skilled in the art upon reference to the description. It is, therefore, intended that the appended claims encompass any such modifications or embodiments.

What is claimed is:

1. A grading lamp for gemstones comprising:
   a base having an open top with a bottom wall bounded by upstanding front, rear, and side walls, and a lid hinged to the rear wall for swinging between open, intermediate, and closed positions relative to the base, the lid having an upper surface and a lower surface with front and rear flanges;
   a light positioned on the lower surface, the light being a natural daylight;
   a tray disposed within the open top of the base, the tray including a plurality of reference stone receptacles configured to accept a respective plurality of color reference stones;
   an examination receptacle disposed within the tray, the examination receptacle sized to accept at least a gem under examination;
   the closed position configured to provide reference stone space contact between the lower surface and the tray such that the plurality of color reference stones are held in place within the respective depressed reference stone receptacles within the grading lamp;
   the intermediate position configured to mitigate at the examination receptacle ambient light sourced outside of the grading lamp and to block at the examination receptacle direct overhead light sourced outside of the grading lamp; and
   the intermediate position configured to provide at the examination receptacle direct light from the light.

2. The grading lamp as recited in claim 1, wherein the intermediate position comprises the lid being from about 25 degrees to about 65 degrees with respect to the base.

3. The grading lamp as recited in claim 1, wherein the tray further comprises a white color.

4. The grading lamp as recited in claim 1, wherein the tray further comprises UV-inhibiting composition.

5. The grading lamp as recited in claim 1, wherein the examination receptacle is sized to accept at least a gem under examination and two color reference stones.

6. The grading lamp as recited in claim 1, wherein the plurality of reference stone receptacles further comprise a plurality of depressed cones.

7. The grading lamp as recited in claim 6, wherein the depressed cones are configured to hold the color reference stones at an approximately 45 degree angle.

8. The grading lamp as recited in claim 6, further comprising respective labels E, F, G, H, I, J, K, L, M, and N at each of the ten depressed cones.

9. The grading lamp as recited in claim 1, further comprising a channel that interconnects the plurality of reference stone receptacles to provide space to facilitate the insertion and removal of the color reference stones from the grading lamp.

10. The grading lamp as recited in claim 1, wherein the lid further comprises a lamp recess on the lower surface and the light is located within the lamp recess.

11. A grading lamp for gemstones comprising:
    a base having an open top with a bottom wall bounded by upstanding front, rear, and side walls, and a lid hinged to the rear wall for singing between open, intermediate, and closed positions relative to the base, the lid having an upper surface and a lower surface with front and rear flanges, the lid having a lamp recess therein;
    first and second lights positioned in the lamp recess, the first light being a natural daylight, the second light being an ultraviolet light;
    a light diffusing filter positioned over the lamp recess and the first and second lights, the light diffusing filter configured to disperse light from the first and second lights;
    a tray disposed within the open top of the base, the tray including a plurality of depressed cones configured to accept a respective plurality of color reference stones;
    an examination receptacle disposed within the tray, the examination receptacle sized to accept at least a gem under examination; the closed position configured to provide reference stone space contact between the lower surface and the tray such that the plurality of color reference stones are held in place within the respective depressed cones within the grading lamp;
    the intermediate position configured to mitigate at the examination receptacle ambient light sourced outside of the grading lamp and to block at the examination receptacle direct overhead light sourced outside of the grading lamp; and the intermediate position configured to provide at the examination receptacle direct light from the first and second lights.

12. The grading lamp as recited in claim 11, wherein the intermediate position comprises the lid being from about 25 degrees to about 65 degrees with respect to the base.

13. The grading lamp as recited in claim 11, wherein the tray further comprises a white color.

14. The grading lamp as recited in claim 11, wherein the tray further comprises UV-inhibiting composition.

15. The grading lamp as recited in claim 11, wherein the examination receptacle is sized to accept at least a gem under examination and two color reference stones.

16. The grading lamp as recited in claim 11, wherein the depressed cones are configured to hold the color reference stones at an approximately 45 degree angle.

17. The grading lamp as recited in claim 11, further comprising respective labels E, F, G, H, I, J, K, L, M, and N at each of the ten depressed cones.

18. A grading lamp for gemstones comprising:
a base having an open top with a bottom wall bounded by upstanding front, rear, and side walls, and a lid hinged to the rear wall for swinging between open, intermediate, and closed positions relative to the base, the lid having an upper surface and a lower surface with front and rear flanges, the lid having a lamp recess therein;
first and second lights positioned in the lamp recess, the first light being a natural daylight, the second light being an ultraviolet light;
a light diffusing filter positioned over the lamp recess and the first and second lights, the light diffusing filter configured to disperse light from the first and second lights;
a tray disposed within the open top of the base, the tray including ten depressed cones configured to accept a respective ten color reference stones, the tray including a UV-inhibiting composition providing a white color;
a channel interconnecting the ten depressed cones to provide space to facilitate the insertion and removal of the color reference stones from the grading lamp;
an examination receptacle disposed within the tray, the examination receptacle sized to accept at least a gem under examination and two color reference stones;
the closed position configured to provide reference stone space contact between the lower surface and the tray such that the plurality of color reference stones are held in place within the respective depressed cones within the grading lamp;
the intermediate position being from about 25 degrees to about 65 degrees with respect to the base;
the intermediate position configured to mitigate at the examination receptacle ambient light sourced outside of the grading lamp and to block at the examination receptacle direct overhead light sourced outside of the grading lamp; and
the intermediate position configured to provide at the examination receptacle direct light from the first and second lights.

* * * * *